United States Patent [19]

Foley et al.

[11] Patent Number: 4,684,618

[45] Date of Patent: Aug. 4, 1987

[54] BIMETALLIC CATALYSTS FOR THE REACTION OF CARBON MONOXIDE AND HYDROGEN AND METHOD OF MAKING THE CATALYSTS

[75] Inventors: Henry C. Foley, East Norwalk; Michael P. O'Toole, Stamford, both of Conn.

[73] Assignee: American Cyanamid Company, Stamford, Conn.

[21] Appl. No.: 791,648

[22] Filed: Oct. 28, 1985

[51] Int. Cl.[4] .......................... B01J 21/04; B01J 23/64
[52] U.S. Cl. ..................................... 502/313; 518/714
[58] Field of Search ......................... 502/313; 518/714

[56] References Cited

U.S. PATENT DOCUMENTS 4,096,164  6/1978  Ellgen et al. ................... 260/449 R
4,328,129  5/1982  Huang ................................. 502/316

Primary Examiner—W. J. Shine
Attorney, Agent, or Firm—Gordon L. Hart

[57] ABSTRACT

For the reaction of CO and $H_2$ to produce hydrocarbons and alcohols, catalysts prepared by depositing carbonyls of molybdenum or tungsten and rhodium or ruthenium on alumina support and decomposing and oxidizing the carbonyls to oxides of the metals on the support.

2 Claims, No Drawings

BIMETALLIC CATALYSTS FOR THE REACTION OF CARBON MONOXIDE AND HYDROGEN AND METHOD OF MAKING THE CATALYSTS

The invention relates to improvements in catalysts for the catalytic reaction of carbon monoxide and hydrogen to produce hydrocarbons and oxygenated compounds, and to the use of such catalysts in such reactions. The invention provides improved catalysts and an improved method of making such catalysts and an improved process using such catalysts.

There is much prior art relating to catalysts for use in the Fischer-Tropsch synthesis. More particularly, catalysts having a combination of a Group VI B metal, e.g. Mo or W with a Group VIII metal, e.g. Rh or Ru, on alumina supports have been described for use in such reactions.

U.S. Pat. No. 4,210,597 described use of rhodium tungsten catalysts with some sodium in the catalyst to promote oxygenation and decrease methanation, with the result that yields of the lower aliphatic acid and alcohol products were improved. Using the same catalyst but without sodium caused the production of hydrocarbons to predominate with only minimal oxygenated products. The patent stated and demonstrated that without sodium, the rhodium-tungsten catalyst described would be fairly active for producing hydrocarbons but would have little or no activity for producing the more valuable oxygenated compounds.

Use of manganese or iron with Rh-Mo or Rh-W as catalyst for the reaction of $H_2$ with CO to favor the production of two-carbon oxygenation products, was described in U.S. Pat. No. 4,096,164.

One object of the invention is to provide a method of making catalysts for the catalytic reaction of CO and $H_2$, and the catalysts so made, which can produce conversion selectively to methanol and ethanol as oxygenate products. Most of the remaining conversion products are the hydrocarbon products of methanation.

Another object is to provide a method of making catalysts comprising molybdenum or tungsten and rhodium or ruthenium on an alumina support, and the catalysts so made, which can produce significant oxygenate yields without the need for addition of other elements such as sodium or manganese or iron.

Catalysts of the invention are prepared by impregnating an alumina catalyst support with compounds of Mo or W and Rh or Ru. The alumina support is preferably a precipitated alumina, for example Cyanamid's Aero, α-$Al_2O_3$ having nominal surface area of 270 $m^2$/gm and pore volume of 0.6 cc/gm. Other useful supports of α-$Al_2O_3$ include Alumoxide-C, (Degussa) and Catapal-B (Conoco) prepared by hydrolysis of the alkoxides or halides of alumina. Useful alumina supports may include other ingredients in minor proportions, in addition to alumina as the principal ingredient, such as silica, magnesia, zirconia, titania, etc. in amounts up to about 5 percent by weight. Other alumina supports having surface areas of about 200–300 $m^2$/gm, pore volumes of about 0.4 to 0.8 cc/gm and impurity levels of less than 0.1 to 1 percent by weight are also suitable for use in the invention. The catalyst support may be in the form of alumina powder or shaped alumina particles.

The preparation of the catalysts, and particularly the method of depositing the metals on the support, are important to the catalytic activity and selectivity of conversion that are obtained when the catalyst is used in the catalytic process. A carbonyl compound of the selected molybdenum or tungsten metal is dissolved in an organic solvent, and the alumina support is impregnated by slurrying particulate alumina in the solution and refluxing the slurry for a time sufficient to chemisorb the metal carbonyl on the alumina. The carbonyl is then decomposed and oxidized on the alumina, leaving the metal oxide dispersed on the surface area of the alumina in an amount from 1 to 10 percent by weight of the catalyst.

The carbonyl of the selected rhodium or ruthenium metal is similarly deposited, decomposed and oxidized on the same support, leaving Rh or Ru oxide dispersed on the alumina support which had been previously impregnated with the oxide of Mo or W is slurried in a solution of Rh or Ru carbonyl. Subsequent oxidation and decomposition of the carbonyl on the support leads to deposition of the metal oxide of Rh or Ru over the oxide of Mo or W on the support. The Rh or Ru oxide is thus deposited in an amount from 0.5 to 5 percent by weight of the catalyst using the same procedure that was previously used to deposit the Mo or W oxide.

The catalysts can also be prepared as follows. A carbonyl compound of the selected molybdenum or tungsten metal is dissolved in an organic solvent. The alumina support is impregnated by slurrying particulate alumina in the solution and refluxing the slurry for time sufficient to chemisorb the metal carbonyl on the surface area of the alumina. The carbonyl of the selected rhodium or ruthenium metal is then similarly deposited on the same particles onto which the metal carbonyl of Mo or W was previously chemisorbed. Those particles are slurried in a carbonyl solution of Rh or Ru and the slurry is refluxed for time sufficient to chemisorb the metal carbonyl of Rh or Ru. Subsequent decomposition and oxidation of the carbonyls of the two metals on the support leads to formation of Rh or Ru oxide over the oxide of Mo or W on the support.

It is important to deposit the W or Mo before the Rh or Ru is deposited. The use of metal carbonyl solutions for deposition of the metals is also important. By these procedures we obtain a unique surface epitaxy of the second metal oxide deposited over the first on the support.

The molybdenum or tungsten oxide is bound strongly to the surface of the alumina support through shared oxygen atoms as an epitaxial layer. The rhodium or ruthenium oxide is bound in turn to the molybdenum or tungsten oxide on the support. The molybdenum or tungsten oxide anchors the rhodium or ruthenium oxide to the support. The catalytic metals are thus evenly dispersed over the surface area of the support in a unique surface epitaxial structure. We believe this unique surface epitaxy of the catalytic metals results from the method of making the catalyst and accounts for the good yields and good selectivity of conversion to methanol and ethanol products which can be obtained even under mild conditions using these catalysts in the process of the invention.

The invention is described in more detail in detailed examples below, which demonstrate advantages of the invention. By using higher operating pressures for the catalytic reaction than those used in the examples, one may produce even higher conversions with as good or better yields of the oxygenate products.

EXAMPLE 1

A solution of 3.684 g. $W(CO)_6$ in 150 ml heptane is prepared. Alumina is prepared by heating precipitated alumina powder in a stream of air at 300° C. for 90 minutes. A slurry is made with 30 grams of the prepared alumina in the tungsten carbonyl solution. The slurry is refluxed for two hours in a flow of nitrogen, then cooled and vacuum filtered. The filtered solids are dried in air at 120° C. The tungsten carbonyl has decomposed leaving an oxide of tungsten dispersed on the alumina support. Then a five gram aliquot of this material is slurried in a solution of 0.326 g. $Ru_3(CO)_{12}$ in 100 ml heptane. The slurry is refluxed under nitrogen for two hours then cooled, vacuum filtered and dried in air at 120° C. The ruthenium carbonyl has been deposited and converted to oxide of ruthenium over an oxide of tungsten, on the support. The finished catalyst is nominally 3% Ru-6% $W/Al_2O_3$.

EXAMPLE 2

A solution of 5.319 g. $Mo(CO)_6$ in 150 ml heptane is prepared. Alumina powder is prepared by heating in a stream of air at 300° C. for 90 minutes. A slurry is made with 30 grams of the prepared alumina in the tungsten carbonyl solution. The slurry is refluxed for two hours in a flow of nitrogen, then cooled and vacuum filtered. The filtered solids are dried in air at 120° C. The molybdenum carbonyl has decomposed leaving an oxide of molybdenum dispersed on the alumina support. Then a ten gram aliquot of this material is slurried in a solution of 0.652 gms of $Ru_3(CO)_{12}$ in 100 ml heptane. The slurry is refluxed under nitrogen for two hours then cooled, vacuum filtered and dried in air at 120° C. The ruthenium has been deposited as ruthenium oxide over the molybdenum oxide on the support. The finished catalyst is nominally 3% Ru-6% $Mo/Al_2O_3$.

EXAMPLE 3

A solution of 0.355 g. $Mo(CO)_6$ in 100 ml heptane is prepared. Alumina is prepared by heating in a stream of air at 300° C. for 90 minutes. A slurry is made with 2 g. of the prepared alumina in the molybdenum carbonyl solution. The slurry is refluxed for two and one half hours in a flow of nitrogen, and cooled to room temperature. Under a purge of nitrogen 0.156 g. of $Rh(CO)_2$ (acetylacetonate) is added to the slurry. The resultant slurry is refluxed in a flow of nitrogen for an additional hour then cooled, vacuum filtered and dried in air at 120° C. The rhodium has been deposited as the carbonyl over the molybdenum carbonyl and both are decomposed in air leaving oxide of rhodium over an oxide of molybdenum, on the support. The finished catalyst is nominally 3% Rh-6% $Mo/Al_2O_3$.

EXAMPLE 4

A solution of 0.246 g. $W(CO)_6$ in 100 ml heptane is prepared. Alumina is prepared by heating in a stream of air at 300° C. for 90 minutes. A slurry is made with 2 g of the prepared alumina in the tungsten carbonyl solution. The slurry is refluxed for two and one half hours in a flow of nitrogen, and cooled to room temperature.

Under a purge of nitrogen 0.156 g. of $Rh(CO)_2$ (acetylacetonate) is added to the slurry. The resultant slurry is refluxed in a flow of nitrogen for an additional hour then cooled, vacuum filtered and dried in air at 120° C. The rhodium has been deposited as an oxide of rhodium over an oxide of tungsten, on the support. The finished catalyst is nominally 3% Rh-6% $W/Al_2O_3$.

EXAMPLE 5

A $Ru/Al_2O_3$ control sample is prepared by slurrying 3.22 g. $Al_2O_3$ in a solution of 0.21 g. $Ru_3(CO)_{12}$ in 100 ml heptane and refluxing the slurry under $N_2$ for two hours. The slurry is then filtered and dried in air yielding a catalyst of nominally 3% $Ru/Al_2O_3$.

EXAMPLE 6

Catalysts prepared in Examples 1 to 5 are used as catalysts for the reaction of the syngas mixture of $H_2$ and CO by the following procedure. 0.5 $Cm^3$ of 40×80 mesh of the catalyst sample are packed into a fixed-bed microreactor capable of operating at 1 to 5 atmospheres total pressure. The catalysts are reduced in situ in flowing hydrogen at 450° C. at atmospheric pressure. The syngas is supplied at a fixed 1:1 ratio in a cylinder of the premixed gases. Gas flow rates are controlled with a calibrated mass flow meter. Gas flows vary from 2 to 20 $cm^3$/min corresponding to 240 to 2400 $hr^{-1}$ respectively. The hydrocarbons, oxygenates, water, carbon dioxide and unreacted feed exit the reactor and are analyzed on-line with two gas chromatographs, suitable for the analysis of hydrocarbons and oxygenates, as well as the $CO_2$, $H_2$ and CO respectively. The results of these experiments with each of the catalysts in Examples 1 to 5 are presented in Tables I and II.

The catalysts of this invention are shown to have both high activity for the conversion of CO and hydrogen to hydrocarbons and an ability to also produce a significant yield of oxygenated products, especially methanol and ethanol, under very mild process conditions.

In addition to the production of significant yields of hydrocarbons and oxygenate when using catalysts according to the invention, as shown in Table II, hydrocarbons which are produced by the syngas reaction with these catalysts are found to contain generally higher proportions of aliphatic hydrocarbons having 2 to 6 carbon atoms, and those aliphatics are found to contain generally higher proportions of olefin to paraffin hydrocarbons, as compared in Table I with reaction products from processes that use catalysts of only ruthenium or only rhodium on alumina, without molybdenum.

TABLE 1

| Catalyst | Pressure (atm.) | Reactor Temp. (°C.) | % C* Conv. | $C_2=/C_2$ | $C_3=/C_3$ | $C_2$ to $C_6/C_1$ |
|---|---|---|---|---|---|---|
| Ru—$Mo/Al_2O_3$ | 1 | 250 | 1.4 | 0.28 | 2.17 | 1.22 |
|  |  | 300 | 2.3 | 0.15 | 1.16 | 0.59 |
|  |  | 350 | 5.9 | 0.06 | 0.40 | 0.44 |
|  | 4 | 250 | 1.0 | 5.56 | 3.97 | 0.96 |
|  |  | 250 | 15.0[a] | 0.03 | 0.32 | 1.02 |
|  |  | 250 | 3.5[b] | 0.17 | 1.85 | 0.61 |
|  |  | 300 | 6.4 | 0.09 | 0.02 | 0.45 |
| Rh—$W/Al_2O_3$ | 1 | 250 | 1.7 | 0.03 | 0.32 | 0.33 |

TABLE 1-continued

| Catalyst | Pressure (atm.) | Reactor Temp. (°C.) | % C* Conv. | $C_2^-/C_2$ | $C_3^-/C_3$ | $C_2$ to $C_6/C_1$ |
|---|---|---|---|---|---|---|
| | | 270 | 2.3 | 0.04 | 0.34 | 0.26 |
| | 4 | 250 | 1.6 | 0.05 | 0.37 | 0.23 |
| | | 270 | 2.1 | 0.06 | 0.38 | 0.25 |
| Rh—Mo/Al$_2$O$_3$ | 1 | 250 | 4.2 | 0.02 | 0.19 | 0.45 |
| | | 270 | 8.0 | 0.01 | 0.07 | 0.39 |
| | 4 | 250 | 5.4 | 0.02 | 0.18 | 0.29 |
| | | 270 | 7.9 | 0.01 | 0.10 | 0.39 |
| Ru/Al$_2$O$_3$ | 1 | 250 | 0.6 | 0.35 | — | 0.38 |
| | | 300 | 1.1 | 0.10 | 1.58 | 0.20 |
| | 4 | 250 | 4.1 | 0.05 | 1.55 | 0.44 |
| Rh/Al$_2$O$_3$ | 1 | 250 | 0.8 | — | 10.30 | 0.87 |
| | | 300 | 3.6 | — | — | 0.24 |
| Ru—W/Al$_2$O$_3$ | 1 | 250 | 1.4 | 0.65 | 6.23 | 1.04 |
| | | 300 | 17.8 | 0.04 | 0.36 | 0.37 |
| | | 350 | 18.0 | 0.04 | 0.28 | 0.30 |
| | 4 | 250 | 3.2 | 0.46 | 6.49 | 0.55 |
| | | 300 | 14.2 | 0.04 | 0.69 | 0.91 |

*GHSV = 2400 hr$^{-1}$
$^{(a)}$GHSV = 480 hr$^{-1}$
$^{(b)}$GHSV = 8658 hr$^{-1}$

TABLE 2

| Example | Catalyst | Temp (°C.) | Pressure (atm.) | % MeOH | % EtOH |
|---|---|---|---|---|---|
| 1 | Ru—W/Al$_2$O$_3$ | 250 | 4 | 3.5 | 2.3 |
| | | 300 | 4 | — | 16.0 |
| 2 | Ru—Mo/Al$_2$O$_3$ | 250 | 4 | — | — |
| | | 300 | 4 | — | — |
| 3 | Rh—Mo/Al$_2$O$_3$ | 250 | 4 | 2.5 | 28.0 |
| | | 270 | 4 | 9.1 | 31.0 |
| 4 | Rh—W/Al$_2$O$_3$ | 270 | 4 | 5.2 | 18.7 |
| 5 | Ru/Al$_2$O$_3$ | 250 | 4 | — | — |
| | | 300 | 5 | — | — |

What is claimed is:

1. Catalyst for the reaction of synthesis gas containing hydrogen and carbon monoxide for selective production of oxygenates comprising a support of alumina which may contain up to about 5% of other oxides, molybdenum or tungsten in the range of 1 to 10 percent by weight deposited as the metal oxide on the surface area of the alumina support by chemisorption from solution and oxidation of molybdenum or tungsten carbonyl on the surface of said alumina and further comprising rhodium or ruthenium in the range 0.5 to 5 percent by weight deposited as the metal oxide by chemisorption from solution and oxidation of the chemisorbed carbonyl of rhodium or ruthenium over said molybdenum or tungsten oxide on the support.

2. A method of making a catalyst having molybdenum or tungsten oxide and rhodium or ruthenium oxide on a catalyst support of alumina, said method comprising adsorbing the carbonyl of molybdenum or tungsten on the surface area of the alumina support and decomposing and oxidizing the adsorbed metal carbonyl to metal oxide, adsorbing the carbonyl of rhodium or ruthenium over the molybdenum or tungsten carbonyl or oxide on the support and decomposing and oxidizing the adsorbed metal carbonyl to metal oxides on the support.

* * * * *